(12) United States Patent
Rai et al.

(10) Patent No.: US 8,535,951 B2
(45) Date of Patent: Sep. 17, 2013

(54) REAGENT FOR DETECTION OF ANALYTE AND PROCESS THEREOF

(75) Inventors: Ganga Prasad Rai, Gwalior (IN); Gauri Shanker Agarwal, Gwalior (IN); Samuel Merwyn Packia Raj, Gwalior (IN); Krishnamurthy Sekhar, Gwalior (IN); Ajay Kumar Sood, Bangalore (IN); Ajay Singh Negi, Bangalore (IN)

(73) Assignees: Director General, Defense Research & Development Organisation, New Delhi (IN); Indian Institute of Science, Bangalore (IN)

( * ) Notice: Subject to any disclaimer, the term of this patent is extended or adjusted under 35 U.S.C. 154(b) by 695 days.

(21) Appl. No.: 12/531,054

(22) PCT Filed: Mar. 13, 2008

(86) PCT No.: PCT/IN2008/000142
§ 371 (c)(1),
(2), (4) Date: Jan. 27, 2010

(87) PCT Pub. No.: WO2008/111095
PCT Pub. Date: Sep. 18, 2008

(65) Prior Publication Data
US 2010/0151485 A1    Jun. 17, 2010

(30) Foreign Application Priority Data
Mar. 14, 2007 (IN) .............................. 542/DEL/2007

(51) Int. Cl.
*G01N 33/549* (2006.01)
(52) U.S. Cl.
USPC ............ 436/532; 436/518; 436/524; 436/527; 436/536; 436/164; 435/7.1; 435/288.7
(58) Field of Classification Search
USPC ................. 436/518, 524, 527, 532, 536, 164; 435/7.1, 288.7
See application file for complete search history.

(56) References Cited

U.S. PATENT DOCUMENTS

| | | | |
|---|---|---|---|
| 5,705,353 A * | 1/1998 | Oh et al. | 435/7.92 |
| 6,548,311 B1 * | 4/2003 | Knoll | 436/524 |
| 2003/0077670 A1 * | 4/2003 | Cheng et al. | 435/7.5 |

FOREIGN PATENT DOCUMENTS
WO    2004/047721    *  6/2004

* cited by examiner

*Primary Examiner* — Melanie Y Brown
(74) *Attorney, Agent, or Firm* — Kilpatrick Townsend & Stockton LLP

(57) ABSTRACT

The present disclosure provides a reagent for detection of analyte in a sample and process of preparation of the reagent. The reagent comprises heparin and substrate coated with the analyte-counterpart. The analyte-counterpart of the reagent is capable of binding to said analyte. The present disclosure further provides a process for detection of an analyte in a sample by contacting said sample with said reagent and detecting formation of analyte-analyte counterpart complex. The present disclosure provides a kit for detection of an analyte in a sample.

9 Claims, 5 Drawing Sheets

REAGENT FOR DETECTION OF ANALYTE AND PROCESS THEREOF

CROSS-REFERENCE TO RELATED APPLICATIONS

The present application is a U.S. National Phase of PCT/IN2008/000142, filed Mar. 13, 2008, which claims the benefit of Indian Patent Application No. 542/DEL/2007, filed Mar. 14, 2007, both of which are incorporated herein by reference.

TECHNICAL FIELD

The present disclosure provides a reagent comprising heparin for detection of an analyte in a sample and process of preparation of said reagent. The present disclosure further provides process for detection of an analyte using said reagent.

BACKGROUND

Typhoid is an endemic febrile disease caused by *Salmonella typhi*. Typhoid is a major concern of public health. The organism usually enters the body by consumption of contaminated food or water and penetrates the intestinal wall. After that it multiplies and enters blood stream within 24-72 hours resulting in enteric fever and bacteremia. After an incubation period of 10 to 14 days, early symptoms of typhoid, like headache, fever, loss of appetite, bradycardia, splenomegaly etc. appear. Typhoid in most cases is not fatal. Antibiotics, such as ampicillin, chloramphenicol, trimethoprim-sulfamethoxazole, and ciprofloxacin, have been commonly used to treat typhoid in developed countries. Prompt treatment of the disease with antibiotics reduces the case-fatality rate to approximately 1%. When left untreated, typhoid fever persists for three weeks to a month. Death occurs in between 10% and 30% of untreated cases. Typhoid is diagnosed either by blood culture or by detection of its antigens or by the detection of its antibodies in the blood.

There are a number of limitations associated with diagnosis by widal test. The widal test is not specific as it cross reacts with other febrile organisms and many organisms of family Enterobacteriaceae. Further, as typhoid is an endemic disease, therefore, there always exists some background level of antibody in the endemic areas which gives misleading results in the widal test. Hence, it becomes necessary to determine the cut-off titer for each region to rule out the possibility of diagnosis as false positive. Further, the widal test gives positive results only after one or two weeks of the onset of fever. The widal test is that test is to be performed on paired serum samples taken at an interval of at least one week apart because single widal test is elusive and inconclusive.

Further limitation of the widal test is that the antibiotic administration in the early phase of infection, inhibits the development of the antibody and hence test may give false negative result. A further limitation of the widal test is that TAB vaccinated normal healthy persons give false positive reaction in widal test due to presence of circulating antibody against vaccine in human system. Another limitation of the widal test is that it gives indirect evidence of typhoid infection. Further limitation of the widal test is that the test has low sensitivity and low specificity.

Other technique known for diagnosis of typhoid is based upon isolation and identification causative agent. This procedure is termed as golden standard. In this technique *Salmonella typhi* is isolated from blood and identified by microscopic and biochemical test. However, this technique has many limitations. One limitation of the above technique is that it is time consuming as it requires long period of incubation from 3 days to 14 days and also requires elaborate laboratory facilities. Another limitation of the above technique is that for its performance large quantity of blood sample (10 ml/patient) is required. Yet another limitation of the above technique is that it needs large volume of culture medium i.e. 100 ml (10 times of blood sample). Still another limitation of the above technique is its low sensitivity (40 to 80%), as there are very few organisms in circulation, as low as 1/ml which leads to false negative results.

Further limitation of above method is that bacterial growth in culture is inhibited by serum bactericidal agents, present in blood which may lead to false negative results. Still further limitation of blood culture is that antibiotics treatment during early phase of infection may inhibit bacterial growth in culture which may give false negative results. WO2004047721 patent provides a process for the preparation of an agglutination reagent for rapid detection of typhoid. WO2007034508 provides an ultra-sensitive method for detection and/or quantification of an analyte in a sample.

Other known techniques such as Radioimmunoassay (RIA), Enzyme-linked immunosorbent assay etc. are based on detection of circulating antigen in the body fluids, but these techniques have many limitations. One limitation of these techniques is that they require sophisticated and elaborate laboratory facilities. Another limitation of RIA is that it requires radioactive material which is health hazard and also needs trained personnel to handle the radioactive material. Still further limitation of above techniques is that reagents are expensive. Further limitation of these techniques is that minimum 4-5 hours are required to perform the tests. There is a large number of latex particle based immunoassay tests used for diagnostic purposes. The presence of antigen is often determined by the agglutination of the antibody coated particles. The tests are reliable up to a finite concentration of the antigen. Below a certain concentration of antigen, the agglutination does not occur. The agglutination is a diffusion governed process and hence quite slow. In order to enhance the rate of agglutination and improve the sensitivity of tests, especially at low concentrations in pico and femto molar range, many techniques have been tried, some of which are discussed below.

The non-cavitating standing wave ultrasound has been used to increase the sensitivity of different latex agglutination tests because of the increased rate of particle collision as antibody coated particles are forced into the pressure nodal regions (Grundy et al, J of Immunological Methods, vol 165, p 47, (1993) and Ellis et al, J Med. Microbiol., vol 49, p 853, (2000)). Microfluidic systems with controlled flow of small volumes of fluids are another approach to enhance the interaction between antigen and antibodies (Verpoorte, Electrophoresis, vol. 23, p 677, (2002) and Kricka, Clinical Chemistry, vol 44, p 2008, (1998).

Coplanar electric field has also been used to form chains of colloidal particles thereby enhancing the rate of latex agglutination reactions (Song et al, Analytical Chemistry, vol. 66, p. 778, (1994).

All the aforesaid methods of the prior art have their own inherent limitations. For example, in coplanar fields, the particles form chains. In a chain the number of neighbours is at the maximum two. In other words, it is only possible to form arrays of the particles. Hence, in case even if there are more number of binding sites on the antibody coated particle, one can not improve the specificity and sensitivity any further. Microfluidic systems need a lot of precise engineering which is not always available at hand. Thus, there is a need in the art to provide a method and system whereby the sensitivity of the assay is increased and the material in a sample may be detected even at low concentrations.

It is expressly not admitted, however, that any of the documents incorporated by reference herein teach or disclose the present invention.

SUMMARY

The present disclosure provides a reagent for detection of analyte in a sample, said reagent comprising heparin and substrate coated with an analyte-counterpart, wherein the analyte-counterpart is capable of binding to said analyte.

The present disclosure provides a process for detection of an analyte in a sample, said process comprising preparing a suspension of a substrate, coating said substrate with an analyte-counterpart and adding heparin to obtain a reagent, contacting said sample with said reagent, applying electric field in a direction perpendicular to plane of said sample and detecting formation of complex between said substrate coated with said analyte counterpart and said analyte.

The present disclosure provides a kit for detection of an analyte in a sample, wherein the kit comprises the reagent.

BRIEF DESCRIPTION OF ACCOMPANYING DRAWINGS

DETAILED DESCRIPTION

Figure 1:
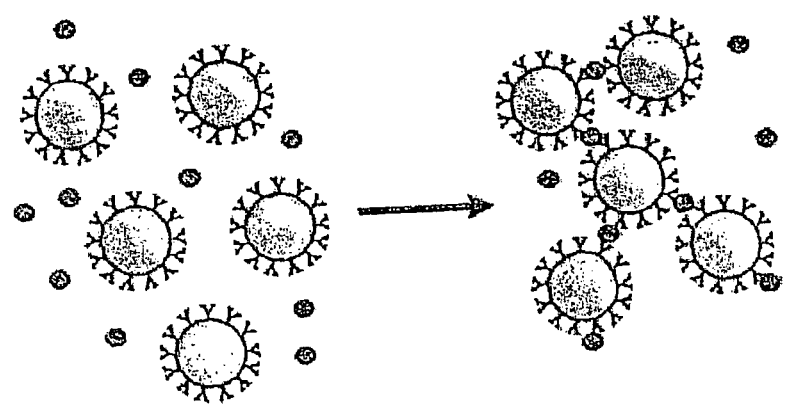
FIG. 1 shows analytes trapped between substrate to which the analyte-counterpart is attached causing them to agglutinate.

The present disclosure provides a reagent for detection of analyte in a sample, the reagent comprising heparin and substrate coated with said analyte-counterpart, wherein the analyte-counterpart is capable of binding to said analyte.

The present disclosure provides a reagent for detection of an analyte in a sample, the reagent comprising heparin and carboxylated latex particles coated with an analyte-counterpart, wherein said analyte-counterpart is capable of binding to said analyte.

The present disclosure provides a process for the preparation of the reagent, the process comprising preparing a suspension of a substrate, coating the substrate with an analyte-counterpart; and adding heparin.

The present disclosure provides a process for detection of an analyte in a sample, said process comprising preparing a suspension of a substrate, coating said substrate with an analyte-counterpart and adding heparin to obtain a reagent, contacting said sample with said reagent, applying electric field in a direction perpendicular to plane of said sample and detecting formation of complex between said substrate coated with said analyte counterpart and said analyte.

The present disclosure provides a kit for detection of an analyte in a sample, wherein the kit comprises the reagent.

The present disclosure provides a kit for detection of an analyte in a sample, said kit comprising the reagent and electrodes, where in the electrodes are a means of applying electric energy to the sample in perpendicular direction and a means for detecting read-out signal.

An antigen (from antibody-generating) or immunogen is a molecule that sometimes stimulates an immune response. Antigens are usually proteins or polysaccharides. This includes parts (coats, capsules, cell walls, flagella, fimbrae, and toxins) of bacteria, viruses, and other microorganisms. Lipids and nucleic acids are antigenic only when combined with proteins and polysaccharides. Non-microbial exogenous (non-self) antigens can include pollen, egg white, and proteins from transplanted tissues and organs or on the surface of transfused blood cells.

In the present disclosure, the term analyte encompasses microbe, enzyme, protein, sugar, toxin, hapten, and other foreign particles. Therefore, term analyte also encompasses antigens. The term 'analyte' as used herein may include any substance which is desired to be detected in a given sample. It may be an antigen, antibody, sugar, hapten, toxin or any other such material. In the present disclosure, the term analyte is exemplified by antigen, *Salmonella typhi* antigen.

In the present disclosure, the singular forms "a", "an", and "the" include plural reference, unless the context clearly dictates otherwise. Thus, for example, a reference to "a substrate" includes a plurality of such substrates, and a reference to "an antibody" is a reference to one or more antibodies and equivalents thereof known to those skilled in the art. Similar syntactical principal also applies to other examples such as analyte, particle, immunoglobulin, analyte-counterpart, and molecule.

The 'sample' used for detection of analyte encompasses urine, saliva, blood, synovial fluid, cerebrospinal fluid and any other biological material, whether natural or synthetic. The results may be read or detected by any detectable signal and observed employing techniques such as chemiluminescence, colour, radioactivity, reflectance, fluorescence, birefringence, changes in optical density (at specific or broad wavelength), measurement of absorbance of the transmitted light (Turbidimetry), measurement of scattered light at a small angle to the forward direction (called Nephelometry), scanning laser microscopy, visual observation and digital imaging.

Antibodies, also known as immunoglobulins are proteins that are found in blood or other body fluids of vertebrates, and are used by the immune system to identify and neutralize foreign objects, such as bacteria and viruses referred to as antigens. In the present disclosure the term antibody and immunoglobulin is used interchangeably hereinafter. The term 'analyte-counterpart' is used to denote any material that is capable of recognizing the analyte. For instance, if the analyte is an antigen, the analyte-counterpart may be an antibody. The 'binding partner' or substrate is any particle or material to which the analyte-counterpart is attached, either by covalent or non-covalent linkages. It includes latex, polystyrene, gold, silver, platinum or any other polymeric or fibroses particles onto which the analyte-counterpart may be attached.

An embodiment of the present disclosure provides a reagent for detection of analyte in a sample, said reagent comprising substrate coated with the analyte-counterpart and heparin, wherein said analyte-counterpart is capable of binding to said analyte. The present disclosure employs heparin to minimize the non-specific reactions in sample such as serum and plasma samples.

Another embodiment of the present disclosure provides a process for preparation of the reagent, said process comprising; preparing a suspension of a substrate, coating said substrate with an analyte-counterpart; and adding heparin.

In an embodiment of the present disclosure, the reagent is selected from the group consisting of urine, saliva, blood, synovial fluid cerebrospinal fluid and other biological material.

In another embodiment of the present disclosure, the substrate is selected from a group consisting of latex particle, metal particle, polymeric particle, carbon particle and silicon particle.

Further, in an embodiment of the present disclosure, the latex particle is carboxylated latex particles.

In an embodiment of the present disclosure, the latex particle is carboxylated latex particles having size in the range of 0.88 to 0.90 µm.

Another embodiment of the present disclosure provides that the analyte is a biological macromolecule.

In another embodiment of the present disclosure provides that the analyte is an antigen.

Another embodiment of the present disclosure provides that the antigen is *Salmonella typhi* antigen.

Yet another embodiment of the present disclosure provides that the analyte-counterpart is an antibody.

Still another embodiment of the present disclosure provides that the antigen is selected from a group comprising microbe, enzyme, protein, sugar, toxin, hapten, and other foreign particles.

Another embodiment of the present disclosure provides that the analyte-counterpart selected from a group consisting of protein and carbohydrate.

Another embodiment of the present disclosure provides that the analyte-counterpart is an antibody.

Another embodiment of the present disclosure provides a process for detection of an analyte in a sample, said process comprising contacting said sample with the reagent, and detecting formation of complex between analyte and the analyte counterpart, herein after said complex is referred to as analyte-analyte counterpart complex. The reagent comprises substrate coated with an analyte-counterpart and heparin, wherein the analyte-counterpart is capable of binding to said analyte.

Further, another embodiment of the present disclosure provides that the process of detection of an analyte in a sample is detected by formation of analyte-analyte counterpart complex. The analyte-analyte counterpart complex is detected by employing detection techniques selected from the group consisting of chemiluminescence, colorimetry, radioactivity, reflectance, fluorescence, birefringence, changes in optical density, turbidimetry, nephelometry, scanning laser microscopy, visual observation and digital imaging.

Still another embodiment of the present disclosure provides that the process of detection of an analyte in a sample employs application of an electric field in a direction perpendicular to plane of electrode inserted in the sample.

In another embodiment of the present disclosure, detection of an analyte in a sample is up to pico molar concentration of the analyte present in said sample.

Another embodiment of the present disclosure provides a kit for detection of an analyte in a sample, the kit comprises the reagent. The reagent comprising heparin and substrate coated with said analyte-counterpart, wherein the analyte-counterpart is capable of binding to said analyte.

Yet another embodiment of the present disclosure provides that the kit further comprises electrodes; a means of applying electric energy to the sample in perpendicular direction and a means for detecting read-out signal.

Further embodiment of the present disclosure provides a kit for detection of *Salmonella typhi* antigen in a sample, the kit comprising the reagent and electrodes, where in the electrode is a means of applying electric energy to the sample in perpendicular direction and a means for detecting read-out signal.

Figure 5:
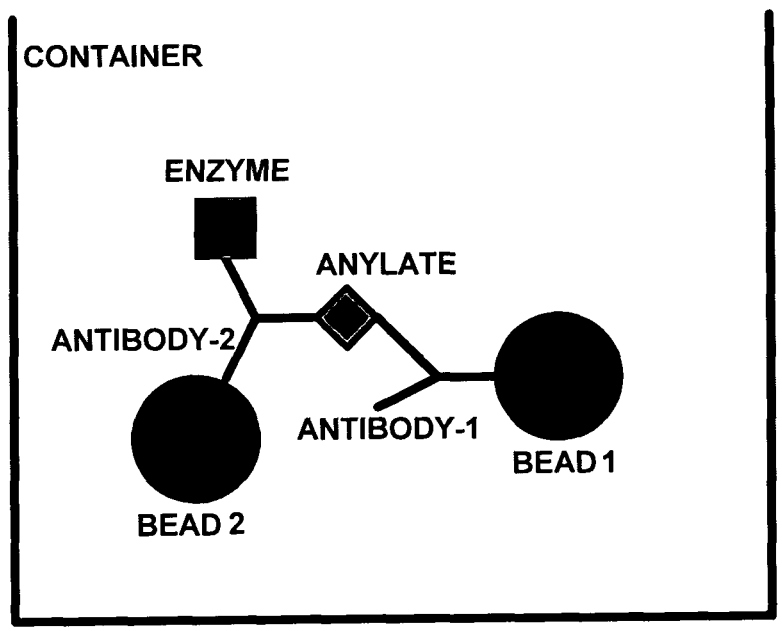
FIG. 5 shows illustration of variant of the method using ELISA for detection of analyte in samples.

Another embodiment of the present disclosure relates to the process for detection of analyte, *Salmonella typhi* antigen in a sample. The present disclosure further provides a highly specific and sensitive method for detection of desired analyte in a sample. The agglutination reaction used for detection of analytes in sample is provided in FIG. 5.

The present disclosure further provides application of electric field in Z direction for detection of analyte in a sample. The electric field enhances the sensitivity of agglutination reaction for detection of analyte, herein exemplified by *Salmonella typhi* antigen.

The process of detection of analyte such as *Salmonella typhi* of the present disclosure comprises the steps of contacting test sample with the reagent of the present disclosure. The reagent comprises substrate such as latex particles coated with antibody against the analyte of interest. The reagent further comprises of heparin. The sample is contacted with the reagent for a period sufficient to cause the analyte-counterpart to bind to analyte. The binding of the analyte present in the sample to the analyte-counterpart results in the formation of analyte-analyte counterpart complex. The complex results in clump formation in the reaction mixture which is then detected. Further, the analyte-analyte counterpart complex is detected by employing detection techniques selected from the group consisting of chemiluminescence, colorimetry, radioactivity, reflectance, fluorescence, birefringence, changes in optical density, turbidimetry, nephelometry, scanning laser microscopy, visual observation and digital imaging.

The process of detection of analyte such as *Salmonella typhi* in the present disclosure optionally employs application of an electric field in a direction perpendicular to the plane of the sample to generate a detectable signal. The application of the electric field results in detection of minute amount of analyte in the sample that cannot be detected otherwise. The application of electric field results is detection of analyte up to pico molar quantity.

The present disclosure provides a highly specific process for detection of analyte such as *Salmonella typhi* antigen in a sample. The sample such as serum sample collected from clinically suspected typhoid patients exhibit non-specific agglutination reaction during testing. Addition of heparin to latex particles coated with analyte counterpart minimizes such non specific interactions and increases the specificity by several folds.

The present disclosure provides a process whereby presence of even minimal amounts of analyte may be detected in a sample. On application of electric field in Z-direction (perpendicular to the plane of the sample) the analyte and analyte-counterpart agglutinate tend to form large clusters in the region of the electric field, leading to detection of even minimal amounts of desired analyte in a given sample.

The present disclosure further provides that under the influence of a perpendicular electric field, the substrate to which the analyte-counterpart(s) is attached, are caused to aggregate, and as a result the analyte is trapped between the substrate. A diagrammatic representation of the mechanism of action is shown in FIG. 1. Since in a cluster, the number of neighbors of a particle is more, this process facilitates the formation of analyte and analyte-counterpart links better and hence gives excellent and very high sensitivity.

The process of detection of analyte in a sample may be implemented through a number of different embodiments such as application of an electric field in the Z-direction. The electric field detects even minimal amounts of the analyte in a sample by using an analyte-counterpart prepared specifically for the analyte. For example, if the analyte is an antigen, then antibodies to that antigen are prepared and kept ready. Thereafter, substrate such as polymeric materials or latex bodies are coated with the said analyte-counterpart prepared, followed by preparation of an admixture comprising the coated material and analyte in the sample. The admixture so prepared is a colloidal dispersion, which is placed on a solid surface (the surface being pre-coated with a conductive material) and subject to an electric field (in Z-direction) such that analyte-counterparts binds to the analyte and the results are detected by an appropriate read-out signal.

Optionally, the unbound bodies and reaction solution may be washed off after a certain period so that only immobilized complexes are left for observation of read-out signal.

Another variant may be an ELISA (enzyme-linked-assay) wherein first analyte-counterpart is attached to a first substrate. A second analyte-counterpart and enzyme attached to a second substrate is also provided. The first analyte-counterpart is introduced into a sample and after some time the second analyte-counterpart is introduced followed by an electric field applied perpendicular to the plane of the sample for a period sufficient to cause the first-analyte-counterpart and second-analyte-counterpart (with enzyme) to agglutinate and produce a detectable readout signal. The diagrammatic representation of the variant of ELISA is provided in FIGS. 5 and 6.

In a variant method, the patient's sample may be collected in vials and analyte-counterpart attached to the substrate is added to the vial. Then two electrodes are dipped into the vial to enable effective formation of analyte-counterpart and analyte complex and development of read-out signal.

In the aforesaid embodiments, the electric field applied may be alternating current or direct current or battery operated.

In another embodiment, the present disclosure provides an apparatus useful for detecting the presence of an analyte in a sample, comprising a conducting electrode and a source of electric energy, including a means for applying electric energy to the electrode in a direction perpendicular to the electrodes. The diagrammatic representation of reaction set up is provided in FIGS. 2 and 6. Antibody coated substrate and the sample containing the analyte is sandwiched between two glass plates (17) coated with conducting indium-tin oxide (ITO) (18). The two plates are separated by insulating spacers of 75 μm thickness and the cell was sealed to prevent evaporation and flow of the suspension. A function generator combined with a potentiometer (25) may be used to regulate the strength of applied sinusoidal voltage which may be read on a multimeter (16). polarising microscope (30) (in transmission mode) combined with CCD video camera (40) may be used to image the particles. The observations are recorded on a video recorder (45). The set up also has a computer (50) which can digitize images at a rate of 25 frames per second. The images captured may be analyzed to quantify the extent of agglutination.

In yet another embodiment, the present disclosure provides a kit for detection of the presence of an analyte in a sample. The kit would vary depending on the kind of test employed. However, in general, the kit may comprise conducting surfaces to act as electrodes; a source and means for applying electric energy to the sample in perpendicular direction to analyte-counterpart and analyte complex; counterpart of analyte capable of recognizing analyte for binding to analyte-counterpart present in sample, wherein the analyte counterpart is coated on substrate such as latex particles; means for detecting read-out signal, and manual of instructions.

An embodiment of the present disclosure provides preparation of the reagent for detection of analyte, *Salmonella typhi* in example 1.

Another embodiment of the present disclosure provides detection of analyte, namely, *Salmonella typhi* antigen in sample with and without use of heparin in Examples 1 and 2. Examples 1 and 2 further provides difference in agglutination observed in fresh and stored test sample during detection of analyte, namely, *Salmonella typhi* antigen. Example 2 further demonstrates the enhancement in the sensitivity of detection on use of electric field perpendicular to plane of electrode inserted in said sample. The agglutination reaction on application of the electric field in the Z direction is greater in intensity than without application of the electric field.

Another embodiment of the present disclosure provides that anticoagulants other than heparin do not prevent non specific interaction that leads to false positive signals. The inability of prevention of non specific interactions at the time of detection of analyte in sample by use of anticoagulants other than heparin such as EDTA and sodium citrate is provided in Example 3.

Another embodiment of the present disclosure provides that agglutination reaction observed in the fresh test samples due to non specific interactions leads to false positive result. Therefore, for accurate detection of presence of analyte in a sample, it is essential to prevent non specific interactions that results in agglutination reaction to eliminate false positive signals. The prevention of non specific interactions is achieved by adding heparin to the substrate such as latex particles coated with analyte counterpart against the analyte of interest. The prevention of non specific interactions in samples by using heparin is the unexpected result of the present disclosure.

While various embodiments and/or individual features of the present invention have been illustrated and described, it would be obvious to those skilled in the art that various other changes and modifications can be made without departing from the spirit and scope of the invention. As will be also be apparent to the skilled practitioner, all combinations of the embodiments and features taught in the foregoing disclosure are possible and can result in preferred executions of the present disclosure.

EXAMPLES

The following examples are put forth so as to provide those of ordinary skill in the art with a complete disclosure and the description of how to make and use the present invention, and are not intended to limit the scope of what the inventors regard as their invention nor are they intended to represent that the experiments below are all and only experiments performed.

EXAMPLES

Example 1

Detection of *Salmonella typhi* Antigen

A. Preparation of Antibody for *Salmonella typhi* Antigen

Flagellin gene sequence specific to *Salmonella typhi* was amplified by polymerase chain reaction (PCR) using gene specific primers. The amplified PCR product was cloned in 6× His-tagged vector and later expressed. The expressed protein was purified by Ni-NTA affinity column chromatography. The protein content of the purified product was determined by Bradford method. Hyper immune serum against this protein was raised in rabbit. Immunoglobulin fraction of hyper immune serum was separated by ammonium sulphate precipitation. The precipitated immunoglobulins was suspended in 1.0 ml PB (50 mM, pH 7.2), dialysed and protein content determined.

B. Preparation of a Suspension Comprising Latex Particles 1.0 ml of 1% carboxylated latex particles and 1.0 ml of 40 mM MES buffer (pH 5.8-6.3) were taken in 2.0 ml micro centrifuge tube and mixed on vortex mixer for 60 sec and centrifuged at 10000 rpm for 10-12 min at a temperature of 4° C. The latex particles were further washed twice in 2.0 ml of 20 mM MES buffer (pH 6.1) by mixing on vortex mixer for 60 seconds and centrifugation at 10000 rpm for 10-12 min. at a temperature of 4° C. Following the final wash, the latex particles were suspended in 1.0 ml MES buffer (20 mM, pH 6.1) and sonicated by a tip sonicator at 5 watts for 60-120 sec. Later 1.0 ml of freshly prepared solution of 0.1 M 1-ethyl-3-(3-dimethylaminopropyl) carbodimide hydrochloride (EDC) in MES buffer (20 mM, pH 6.1) was added drop wise while the solution was slowly vortexed. The tube was rotated slowly end-over-end for 3 hrs at a temperature of 20-25° C. followed by washing 3 times with MES buffer (20 mM, pH 6.1) at 10000 rpm for 10-12 min. at a temperature of 4° C. The latex particles were resuspended in 0.7 ml MES buffer (20 mM, pH 6.1) and sonicated for 60-120 sec by a tip sonicator at 5 watts.

C. Preparation of Latex Reagent

A latex reagent comprises of the latex particles coated with antibody specific against an analyte (which in the present case is *Salmonella typhi*) and heparin.

To this latex particle suspension as prepared above, 0.6 mg of immunoglobulins was added and the volume was made up to 1 ml with MES buffer (20 mM, pH 6.1). This mixture was then rotated end-over-end for 18-20 hrs at a temperature of 20-25° C. for coating the latex particles with the antibodies. The coating reaction was then stopped by addition of 0.06 ml of 1M glycine (pH 11.0). The rotation was continued for 30 min at a temperature of 20-25° C. The latex particles coated with antibody were pelleted out by centrifugation at 10000 rpm for 10-12 min at a temperature of 4° C. The pellet was washed thrice with 2.0 ml of washing buffer (50 mM glycine, pH 8.5, 0.03% triton X-100 and 0.05% sodium azide) at 10000 rpm for 10-12 min at a temperature of 4° C. The washed latex particles coated with antibody were resuspended in storage buffer (50 mM glycine, pH 8.5, 0.03% Triton X-100 and 0.1% sodium azide) to obtain a final concentration of 1% latex coated antibody which was then sonicated with tip sonicator for 60 seconds at 5 watts and stored at 4° C. Heparin was added to above mentioned storage buffer having concentration of 50 units/ml of the storage buffer.

D. Addition of Test Sample to the Latex Reagent 20-40 µl (1 to 2 drops) of fresh test sample, stored test sample, positive control and negative control were placed at distinct places on a glass slide.

Fresh test sample is the sample obtained from subjects and immediately tested for presence of analyte (*S. typhi* antigen).

Stored test sample is sample stored at cold temperatures, at about 4° C. or below for long time (for more than seven days).

10-20 µl (1-2 small drops) of the latex reagent was added to the fresh and the stored test sample, positive and negative controls. The reactants were mixed with separate wooden sticks carefully to avoid any intermixing of reactant placed at separate places on the glass slide. The reactants were further mixed by rotating slide for 1-2 minutes.

E. Determination of Specificity

Antigen detection in above samples was carried out with latex reagents devoid of heparin. All the samples showed agglutination reaction of 1+ grade. However, when latex reagent containing heparin was used, no agglutination (non-specific reaction) was observed in all the samples.

On confirming the result using conventional method of detection of typhoid, it was found that *Salmonella. typhi* antigen was absent in both the fresh and the stored test sample. Therefore, it was concluded that agglutination reaction observed in the fresh test sample and negative control was due to non specific interactions. Therefore, for accurate detection of presence of analyte in a sample, it was essential to prevent non specific interactions that results in agglutination reaction to eliminate false positive signals. The prevention of non specific interactions was achieved by adding heparin to the latex particle suspension coated with antibodies against *S. typhi* antigen.

Example 2

Detection of *Salmonella typhi* Antigen Using Electric Field in Z Direction

The steps of preparation of antibody for *Salmonella typhi* antigen, preparation of a suspension comprising latex particles, preparation of latex reagent, addition of test sample to the latex reagent was carried out as discussed in example 1.

Figure 2:
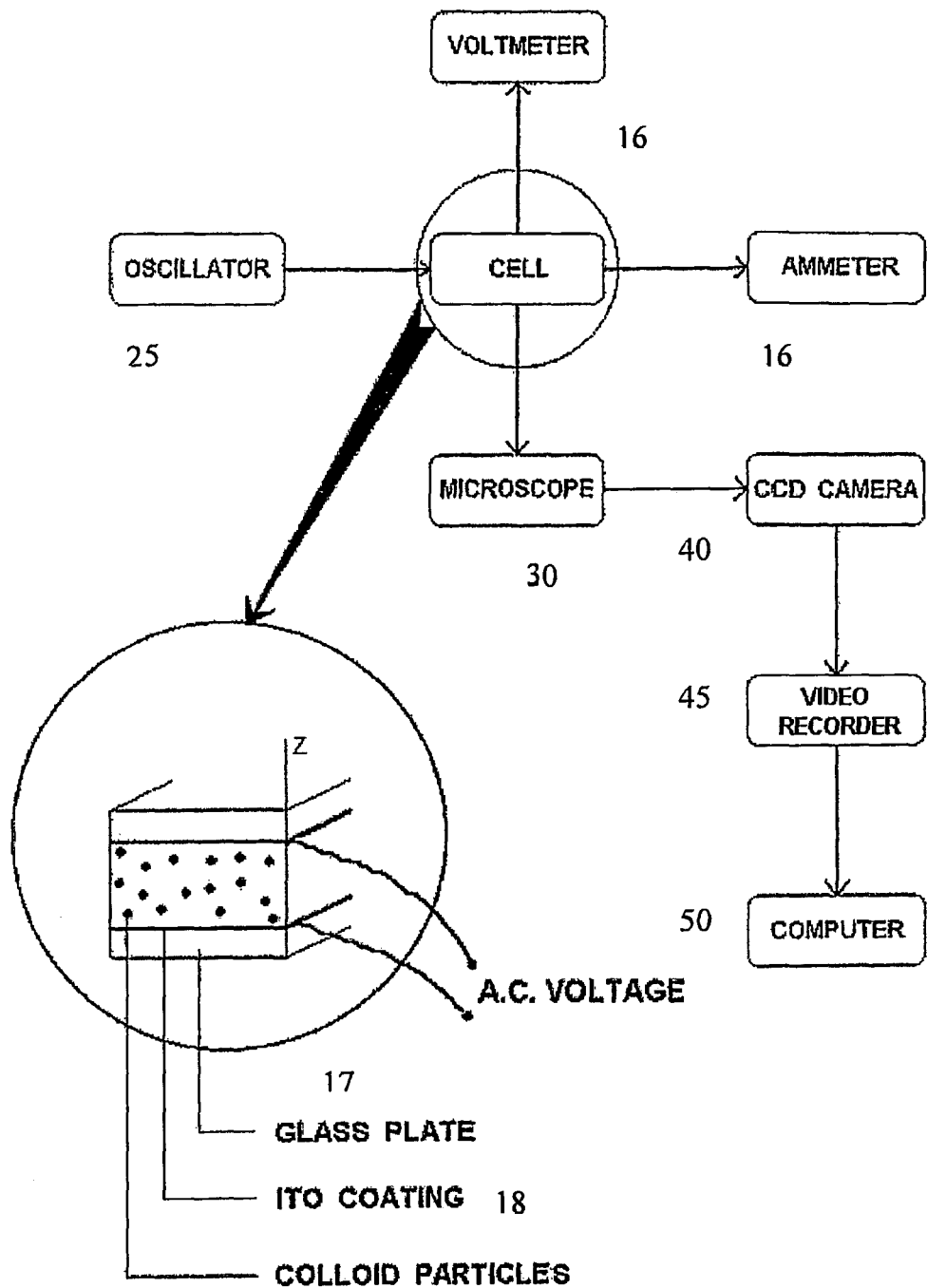
FIG. 2 shows an experimental set up for implementing the invention.
Figure 3:
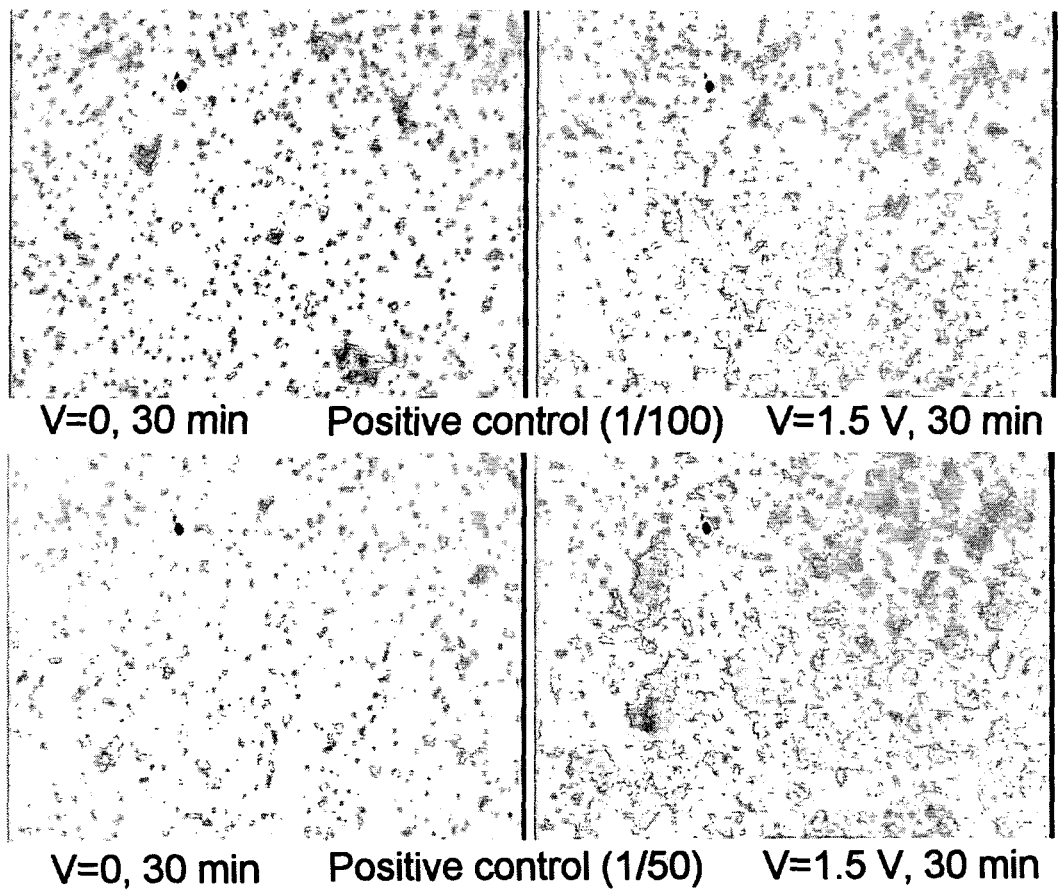
FIG. 3 shows the agglutination of analyte (*Salmonella typhi* antigen) and substrate (latex particles) coated with antibody specific for *Salmonella typhi* in the presence and absence of electric field.
Figure 4:
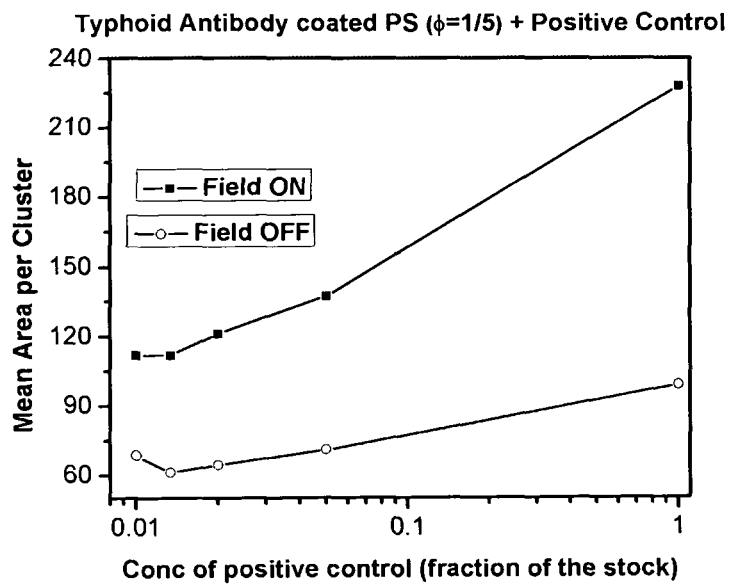
FIG. 4 shows the variation of deviation of pixel intensity with concentration of the positive control.

For application of electric field in Z direction, an example experimental set up is shown in FIG. 2. Suspension of the latex particles and the analyte test sample mixture was sandwiched between two glass plates (17) coated with conducting indium-tin oxide (ITO) (18). The two plates are separated by insulating spacers of 75 µm thickness and the cell was sealed to prevent evaporation and flow of the suspension. A function generator combined with a potentiometer (25) may be used to regulate the strength of applied sinusoidal voltage which may be read on a multimeter (16). A polarising microscope (30) (in transmission mode) combined with CCD video camera (40) may be used to image the particles. The observations are recorded on a video recorder (45). The set up also has a computer with monochrome image grabber card PCI-1411 (National Instruments, USA) (50) which can digitize images at a rate of 25 frames per second. The images captured with this card may be analyzed to quantify the extent of agglutination. To study the effect of electric field, one volume (3 µL) of antibody coated latex particles was mixed with one volume (3 µL) of different dilutions of anylate mixture and this mixture was sandwiched between two indium-tin oxide (ITO) coated glass plates, separated by a spacer of 75 µm thickness. The cell was sealed with wax to prevent evaporation of water. A function generator combined with a potentiometer was used to regulate the strength of the applied electric field. First of all, the threshold electric field for aggregation of particles in the absence of any antigen was determined. An electric field ~0.85 times the threshold field was applied for doing the experiments in the presence of antigen. This choice of the applied field minimizes the false positive (aggregation without antigen) signals while maximizing the sensitivity and rate of recognition. We found that a voltage of 1.5 V was optimal. In order to compare the effect of presence and absence of the electric field, the experiments were also carried out in identical conditions without applying any electric field. A polarizing microscope (in transmission mode with 40× objective) combined with a CCD video camera along with an image grabbing card was used to image the particles. The images thus obtained, were processed using the freely available software ImageJ. After applying appropriate filters and then adjusting the threshold, the images were converted into binary images where the particles/clusters are black and the background is white. Then, using the built in tool in ImageJ, the average area per cluster was calculated. The reaction set up for carrying out the agglutination reaction for detection of analyte in sample is provided in FIG. 6.

Figure 6:
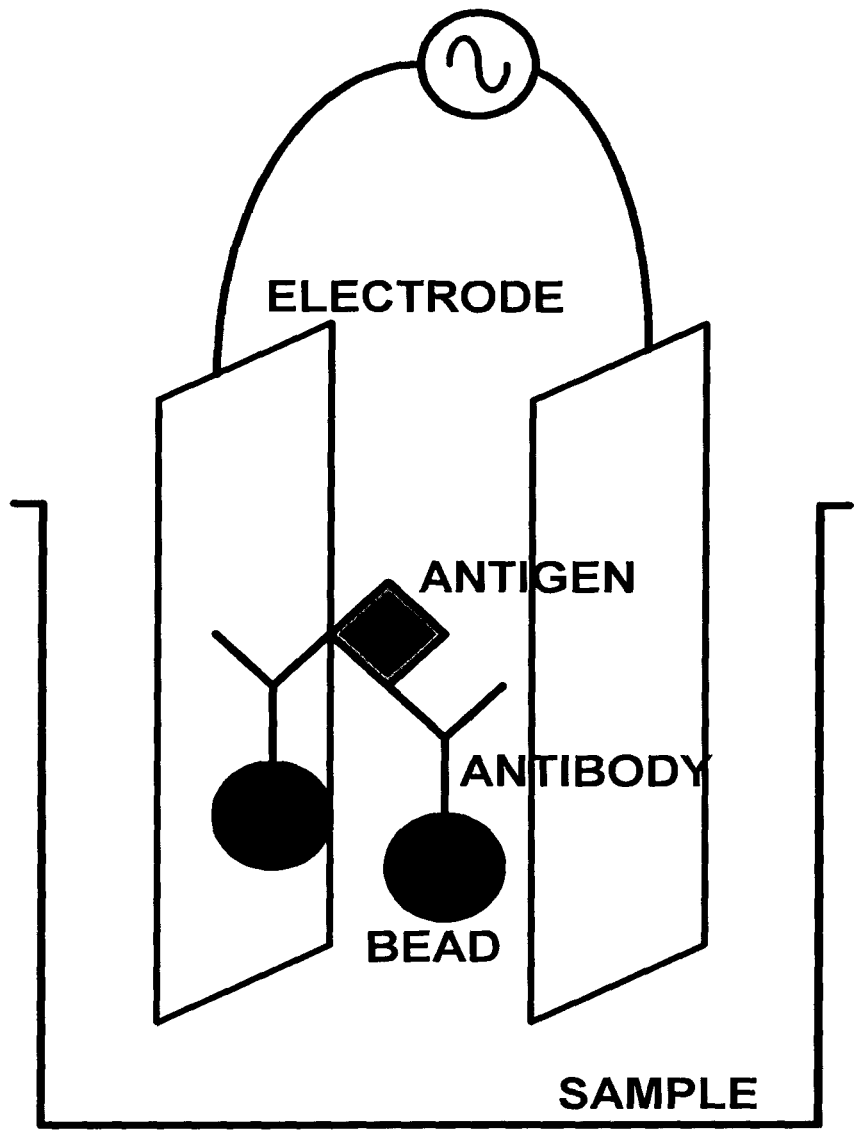
FIG. 6 shows the reaction set up used for detection and quantification of analyte in a sample

FIG. 6 shows use of two electrodes that are dipped into the vial containing the test sample to enable effective agglutination (clump formation of *Salmonella typhi* antigen-antibody complex) reaction. The detection of the analyte is then detected and quantified by using a means of read-out signal.

On application of an electric field to the reaction mixture (test sample and the latex particle suspension comprising heparin), there was agglutination observed in the samples. The agglutination on application of the electric field in the Z direction was greater in intensity than without application of the electric field. The agglutination in the positive control in presence and absence is provided in FIG. 3. In FIG. 3, in the left panels the electric field is absent and in the right panels the field is present. The agglutination reaction is shown for two different concentrations of the positive control.

In addition, the presence of *S. typhi* antigen was quantified by the mean area per cluster method. The graph of variation of mean area per cluster with concentration of positive control is shown in FIG. 4.

Antigen detection in above samples was carried out with latex reagents devoid of heparin. All the samples showed agglutination reaction of 1+ grade. However, when latex reagent containing heparin was used, no agglutination (non-specific reaction) was observed in all the samples.

On confirming the result using conventional method of detection of typhoid, it was found that *S. typhi* antigen was absent in both the fresh and the stored test sample. Therefore, it was concluded that agglutination reaction observed in the fresh and stored test sample and negative control due to non specific interactions. Therefore, for accurate detection of presence of analyte in a sample, it was essential to prevent non specific interactions that results in agglutination reaction to eliminate false positive signals. The prevention of non specific interactions was achieved by adding heparin to the latex particle suspension coated with antibodies against *S. typhi* antigen.

Example 3

Detection of *S. typhi* Antigen in Fresh Test Sample and Stored Test Sample in Presence of Electric Field in the Z Direction and Other Anti-Coagulating Agents The steps mentioned in example 2 are repeated. However, in place of heparin, EDTA was used. Antigen detection in fresh and stored samples, positive and negative controls was carried out with latex reagents devoid of heparin. All the samples showed agglutination reaction of 1+ grade. On addition of EDTA to the latex reagent for detection of *S typhi* antigen, agglutination (non-specific reaction) was observed in all the samples.

On confirming the result using conventional method of detection of typhoid, it was found that *S. typhi* antigen was absent in both the fresh and the stored test sample. Therefore, it was concluded that agglutination reaction observed in the fresh and stored test sample and negative control due to non specific interactions. Therefore, EDTA was not able to prevent non specific interactions that result in agglutination reaction unlike heparin.

The same detection method was carried out in presence of sodium citrate instead of EDTA. Identical result was obtained that suggests that sodium citrate was not able to prevent non specific interactions that results in agglutination reaction and false positive signals unlike heparin.

We claim:

1. A process for detection of an analyte in a sample, said process comprising, a) preparing a suspension of a substrate, coating said substrate with an analyte-counterpart and adding heparin to obtain a reagent, b) contacting said sample with said reagent, c) applying electric field in a direction perpendicular to plane of electrode inserted in said sample thereby concentrating complexes formed by the substrate coated with the analyte counterpart and the analyte and d) detecting formation of the complexes between said substrate coated with said analyte counterpart and said analyte.

2. The process as claimed in claim 1, wherein said complex is detected by employing detection techniques selected from a group consisting of chemiluminescence, colorimetry, radioactivity, reflectance, fluorescence, birefringence, changes in optical density, turbidimetry, nephelometry, scanning laser microscopy, visual observation and digital imaging.

3. The process as claimed in claim 1, wherein said sample is selected from a group consisting of urine, saliva, blood, synovial fluid cerebrospinal fluid and other biological material.

4. The process as claimed in claim 1, wherein said substrate is selected from a group consisting of latex particle, metal particle, polymeric particle, carbon particle and silicon particle.

5. The process as claimed in claim 4, wherein said latex particle is carboxylated latex particle having size in the range of 0.88 to 0.90 μm.

6. The process as claimed in claim 1, wherein said analyte is a biological macromolecule.

7. The process as claimed in claim 1, wherein said analyte is selected from a group consisting of microbe, enzyme, protein, sugar, toxin, hapten, antigen and other foreign particles.

8. The process as claimed in claim 7, wherein said antigen is *Salmonella typhi* antigen.

9. The process as claimed in claim 1, wherein said analyte-counterpart is an antibody.

* * * * *